(12) United States Patent
Makino et al.

(10) Patent No.: US 7,075,076 B2
(45) Date of Patent: Jul. 11, 2006

(54) INSPECTION SYSTEM, INSPECTION METHOD, AND PROCESS MANAGEMENT METHOD

(75) Inventors: Hiroshi Makino, Kokubunji (JP); Hisaya Murakoshi, Tokyo (JP); Hiroyuki Shinada, Mitaka (JP); Hideo Todokoro, Hinode (JP)

(73) Assignee: Hitachi High-Technologies Corp., Tokyo (JP)

( * ) Notice: Subject to any disclaimer, the term of this patent is extended or adjusted under 35 U.S.C. 154(b) by 0 days.

(21) Appl. No.: 10/885,725

(22) Filed: Jul. 8, 2004

(65) Prior Publication Data

US 2005/0051722 A1    Mar. 10, 2005

(30) Foreign Application Priority Data

Sep. 10, 2003    (JP) .............................. 2003-317700

(51) Int. Cl.
*H01J 37/301*    (2006.01)
(52) U.S. Cl. ....................................... 250/310; 250/397
(58) Field of Classification Search ................ 250/310, 250/397
See application file for complete search history.

(56) References Cited

U.S. PATENT DOCUMENTS

| | | | | |
|---|---|---|---|---|
| 6,563,114 | B1* | 5/2003 | Nagahama et al. | 250/310 |
| 6,614,022 | B1* | 9/2003 | Hiroi et al. | 250/310 |
| 6,797,954 | B1* | 9/2004 | Shinada et al. | 250/310 |
| 2003/0127593 | A1* | 7/2003 | Shinada et al. | 250/310 |

FOREIGN PATENT DOCUMENTS

| | | |
|---|---|---|
| JP | 11-037957 | 2/1999 |
| JP | 11-108864 | 4/1999 |
| JP | 2003-202217 | 7/2000 |
| JP | 2000-286310 | 10/2000 |

OTHER PUBLICATIONS

"Imaging Hot-Electron Emission from Metal-Oxide-Semiconductor Structures", Marian Makos et al., Physical Review Letters, vol. 76, No. 17, Apr. 22, 1996; pp. 3200-3203.

"Low-energy Electron Microscopy"; R.M. Tromp, IBM J. Res. Develop., vol. 44, No. 4, Jul. 4, 2000, pp. 503-516.

* cited by examiner

*Primary Examiner*—Kiet T. Nguyen
(74) *Attorney, Agent, or Firm*—Mattingly, Stanger, Malur & Brundidge, P.C.

(57)    ABSTRACT

The present invention relates to an inspection apparatus comprising:
an electron emitting unit for sequentially emitting an electron beam in the direction of the inspection area of a sample;
a decelerating means for drawing back the electron beam in the vicinity of the inspection area;
an imaging unit for forming images of the electron beam, which has been drawn back in the vicinity of the inspection area, on multiple different image forming conditions;
an image detecting unit for capturing the electron beam that formed an image corresponding to each image forming condition and an image processing unit for comparing the images on different image forming conditions with one another to thereby detect a defect in the inspection area.

33 Claims, 11 Drawing Sheets

FIG. 2(a)
FIG. 2(b)
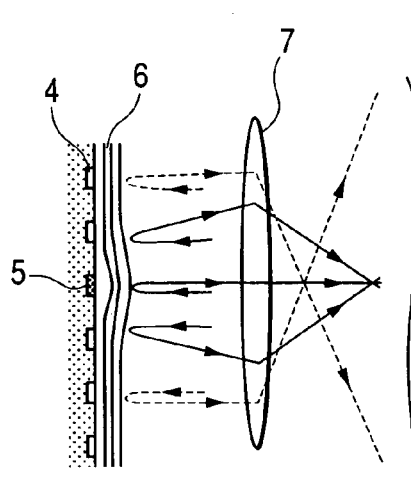
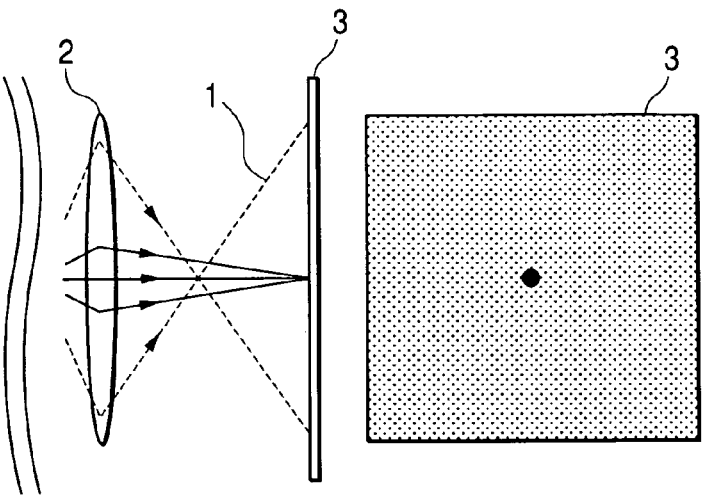
FIG. 3(a)
FIG. 3(b)
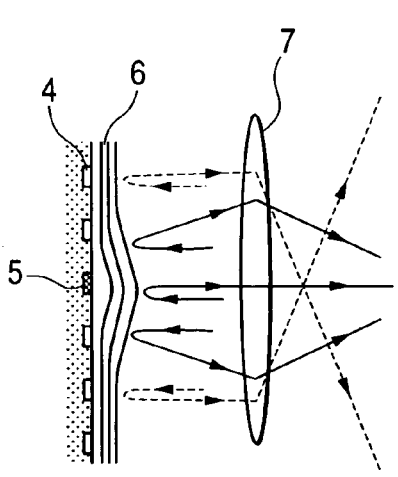
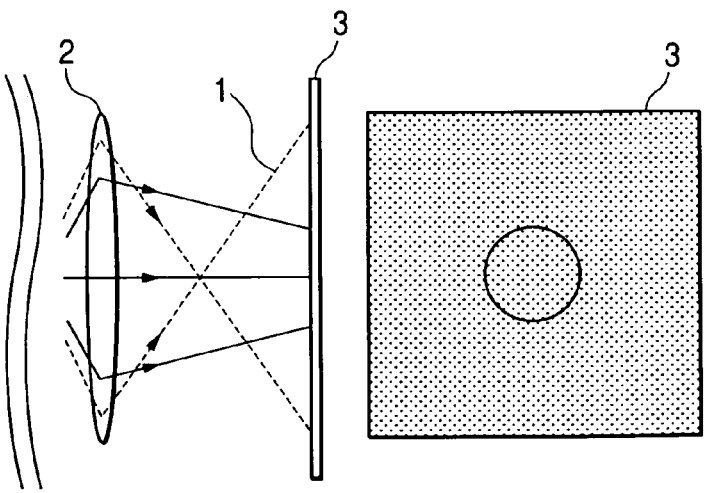

IRRADIATION OF A SHEET
ELECTRON BEAM

PATTERN MODEL OF SIMULATION

RELATION BETWEEN THE POSITION OF THE IMAGING PLANE AND THE BRIGHTNESS OF THE IMAGES

IMAGE SIMULATION RESULTS

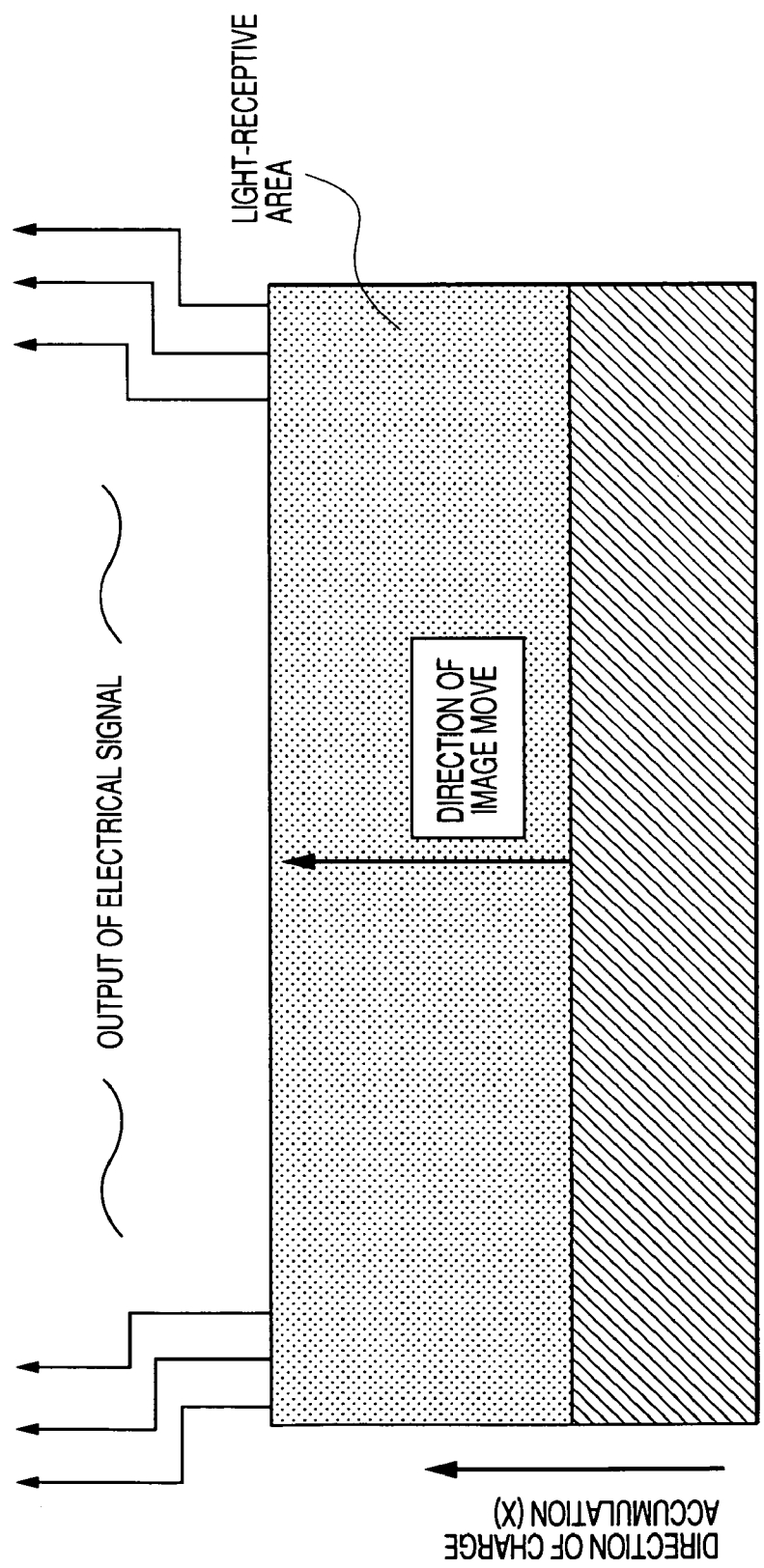

US 7,075,076 B2

INSPECTION SYSTEM, INSPECTION METHOD, AND PROCESS MANAGEMENT METHOD

CLAIM OF PRIORITY

The present application claims priority from Japanese application JP 2003-317700 filed on Sep. 10, 2003, the content of which is hereby incorporated by reference into this application.

FIELD OF THE INVENTION

This invention relates to methods and apparatus for inspection of samples (such as semiconductor devices.).

BACKGROUND OF THE INVENTION

In the manufacturing process of semiconductor devices, as an apparatus for detecting defects in a pattern formed on a wafer 13, a mirror projection inspection apparatus is known, wherein defects are detected by the following step: applying a sheet electron beam on a semiconductor wafer, forming an image of the electron beam drawn back on the surface of the wafer 13 (hereafter referred to as a mirror electron), and comparing the images for the same pattern of different areas. (See, for example, JP11-108864A.)

Here, a mirror projection inspection apparatus will be described with reference to the FIG. 4. FIG. 4 is a schematic drawing of a mirror projection inspection apparatus comprising a cathode 8, a condenser lens 9, a beam separator 10, an objective lens 7, a projection lens 11, an image detecting unit 12, a charge control unit 14, a wafer 13, retarding power supply 18, an image processing unit 17, a lens control unit 15, and a stage control unit 16.

The retarding power supply 18 applies a voltage to the wafer 13 so that the sheet electron beam applied to the wafer 13 is drawn back in the vicinity of the surface of the wafer 13; The lens control unit 15 controls the lens so that the image detecting unit 12 detects the electron beam drawn back in the vicinity of the surface of the wafer 13; and, the stage control unit 16 moves the wafer 13 in synchronization with the capture of images at the image detecting unit 12 so that the sheet electron beam illuminates throughout the inspection area of the wafer 13; the image processing unit 17 identifies defective portions by sequentially comparing the images captured at the image detecting unit 12 for the same patterns lying side-by-side.

This system realizes a substantial improvement in speed of inspection in comparison with a SEM (Scanning Electron Microscopy) type inspection apparatus.

The process of detecting electrical defects (for example open defects) formed on the wafer 13 by a conventional mirror projection inspection apparatus will be illustrated with reference to the attached drawing. FIG. 2(a) schematically illustrates how the mirror electron 1 is formed into an image on the detection plane 3 by an imaging lens 2: the potential of the wafer 13 and the imaging lens 2 are adjusted so that the mirror electron 1 drawn back on the defective portion 5 is formed into an image on the detection plane 3 as a clear contrast. FIG. 2(b) shows an electron density distribution on the detection plane 3, where the mirror electron 1 drawn back on a defective portion 5 converges on the detection plane 3, and the electron drawn back on a normal portion 4 diverges at the detection plane 3. As the result, an image of the defective portion 5 is formed as a bright spot on the detection plane 3. FIG. 3 shows the case where a defective portion 5 is charged to a different potential from the defective portion 5 in FIG. 2, wherein, on the defective portion 5 in FIG. 3, an electric field distribution 6 different from that in FIG. 2 being formed, the mirror electron 1 does not converge on the detection plane 3. FIG. 3(b) shows an electron density on the detection plane 3, wherein, there being no difference in electron density between the defective portion 5 and the normal portion 4, no image of a defect can be formed there. This is also the case with shape defects, when conditions are set for the mirror electron from a targeted defective portion 5 to converge on the detection plane 3, a mirror electron from a defective portion 5 of different size will not converge on the detection plane 3 and it can not be detected. Therefore, when an inspection is conducted by using a conventional mirror projection inspection apparatus, a defect of different size or of different potential from a targeted defect can not detected.

SUMMARY OF THE INVENTION

To solve above mentioned problem, the present invention, applies a sheet electron beam spreading two-dimensionally to multiple areas on a wafer 13 sequentially. More specifically, a preferred embodiment of the present invention relates to a a pattern-defect inspection apparatus, wherein a negative voltage is applied on the wafer 13, and the voltage is adjusted so as for a sheet electron beam to be drawn back from the surface of the wafer 13. Images of the electron drawn back from the wafer 13 (hereinafter called mirror electron 1) are sequentially formed, and such images are sequentially captured by an image detecting unit, and these images are compared with one another thereby to detect a pattern defect formed on the sample, and the images for the same inspection area captured by the image detecting unit are acquired at multiple different focuses.

According to the above embodiment of the present invention a mirror projection inspection apparatus to detect various kinds of defects many he realized.

BRIEF DESCRIPTION OF THE DRAWINGS

FIGS. 2(a) and 2(b) are schematic diagrams illustrating the imaging on a detection plane of a mirror electron drawn back at a defective portion;

FIGS. 3(a) and 3(b) are schematic diagrams illustrating the imaging of a mirror electron drawn back at a defective portion of different potential from the one in FIGS. 2(a) and 2(b);

FIG. 7 is a schematic diagram illustrating the operation principle of the TDI sensor;

DETAILED DESCRIPTION OF THE PRESENT INVENTION

The embodiments of the present invention will be described in detail with reference to the attached drawings.

First Embodiment

Figure 1:
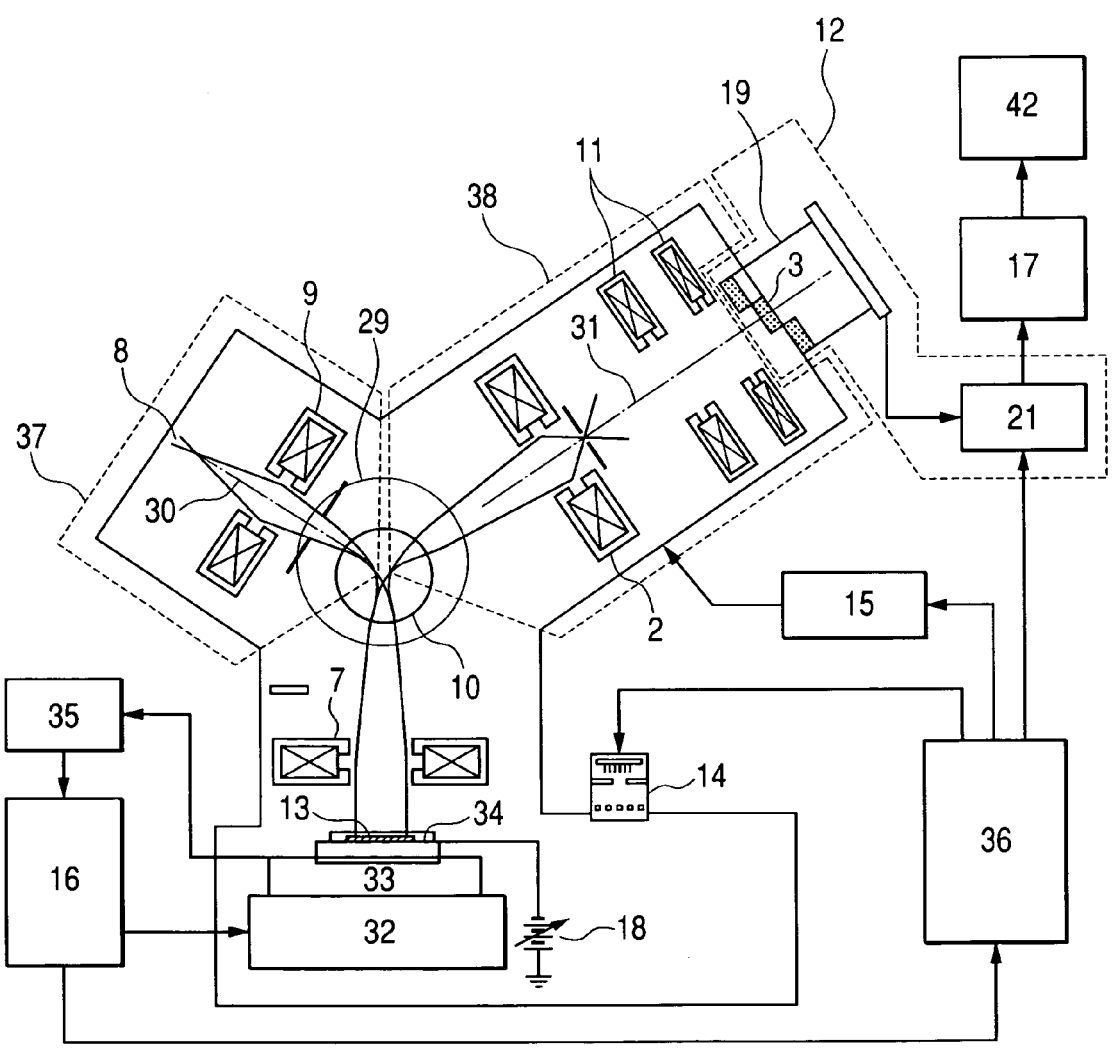
FIG. 1 is a diagram illustrating the configuration of an apparatus as an embodiment of the present invention.
Figure 4:
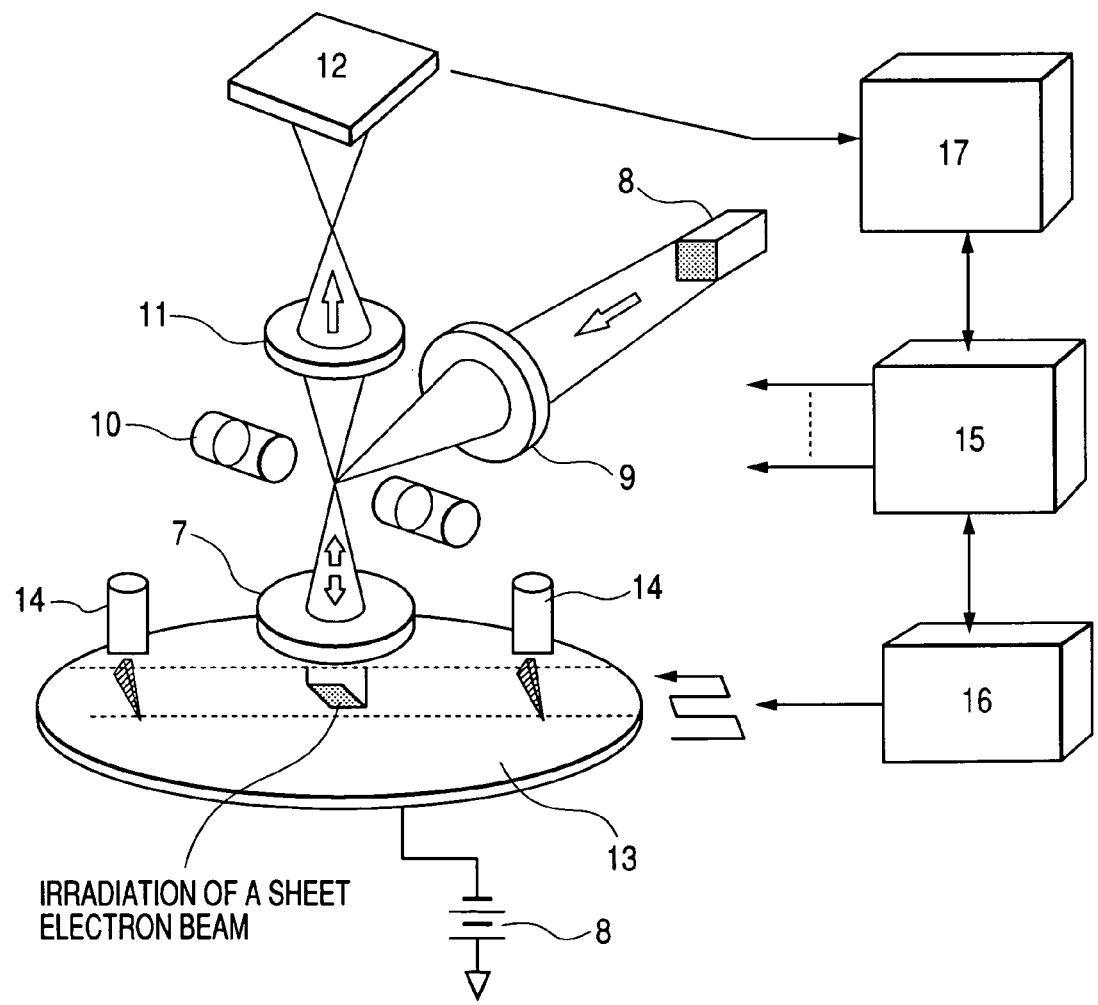
FIG. 4 is a diagram illustrating a basic configuration of a mirror projection inspection apparatus.

The present embodiment illustrates a defect inspection apparatus wherein an image detecting unit comprises multiple detectors 19, each of which captures an image on a different focus of the same inspection area. FIG. 1 illustrates the components for the explanation of the operation principle of an embodiment of the present invention. FIG. 1 comprises mainly an electron illuminating unit 37, an image processing unit 17, a stage controlling unit 16 and a system controlling unit 36. The electron illuminating unit 37 comprises a cathode 8, a condenser lens 9 and an aperture 29, and an electron beam emitted from the cathode 8 is converged by the condenser lens 9 and focuses in the vicinity of a beam separator 10 and on the focal plane of an objective lens 7. This focal plane is determined by magnetization of the objective lens and an action of an electrostatic lens by retarding as explained below. By focusing on this focal plane, an electron beam enters perpendicularly to the sample.

An electron beam is deflected by the beam separator 10 to have an optical axis perpendicular to the wafer 13 (sample). The electron beam deflected by the beam separator 10 is converted into a sheet electron beam uniform in a direction perpendicular to the surface of the wafer 13.

A negative potential approximately equal to or slightly higher than an accelerating voltage of the electron beam is applied to the wafer 13 by a retarding power supply 18 to thereby yield an electric field that corresponds to the shape of a semiconductor pattern formed or the charge thereof on the surface of the wafer 13. This electric field works as a retarding means to repel or drawback the great majority of the electron beam immediately before impingement on the wafer 13 and let it turn back upward with a direction and an intensity reflecting the pattern information of the wafer 13.

The repelled or drawn back electron beam (hereinafter referred to as mirror electron 1) is converged by the objective lens 7, and deflected by the beam separator 10 to be on the optical axis 31 of an imaging unit 38, and through an imaging lens 2 and a projection lens 11 forms on a detector 19 a magnified image of information of partial local potential change or projections and depressions, etc. on the surface of the wafer 13. The detector 19 to detect an image comprises multiple detecting planes 3 which are in relatively different distances from the wafer 13, enabling to obtain an image on a different focus condition on each detecting plane 3. These images are converted to electric signals and transmitted to the image processing unit 17.

With the configuration described above, since an electron beam will not impinge on the sample (wafer 13), a shape defect portion can be detected but an electrical defect portion can not be detected because it is not charged differently from a normal portion 4.

Therefore, the apparatus according to an embodiment of the present invention further comprises a charge control unit 14 for controlling a state of charge of the sample by emitting an electron beam or light prior to capturing images for inspection, thus conducting an inspection after pre-charging the wafer 13 to a predetermined potential.

By thus controlling the charge of the wafer, it is now possible to have on the wafer surface a distribution of potential reflecting electrical defects (such as short-circuit defects and open defects) not only on the surface but also inside of a pattern, thereby enabling identification of these defects.

Figure 5:
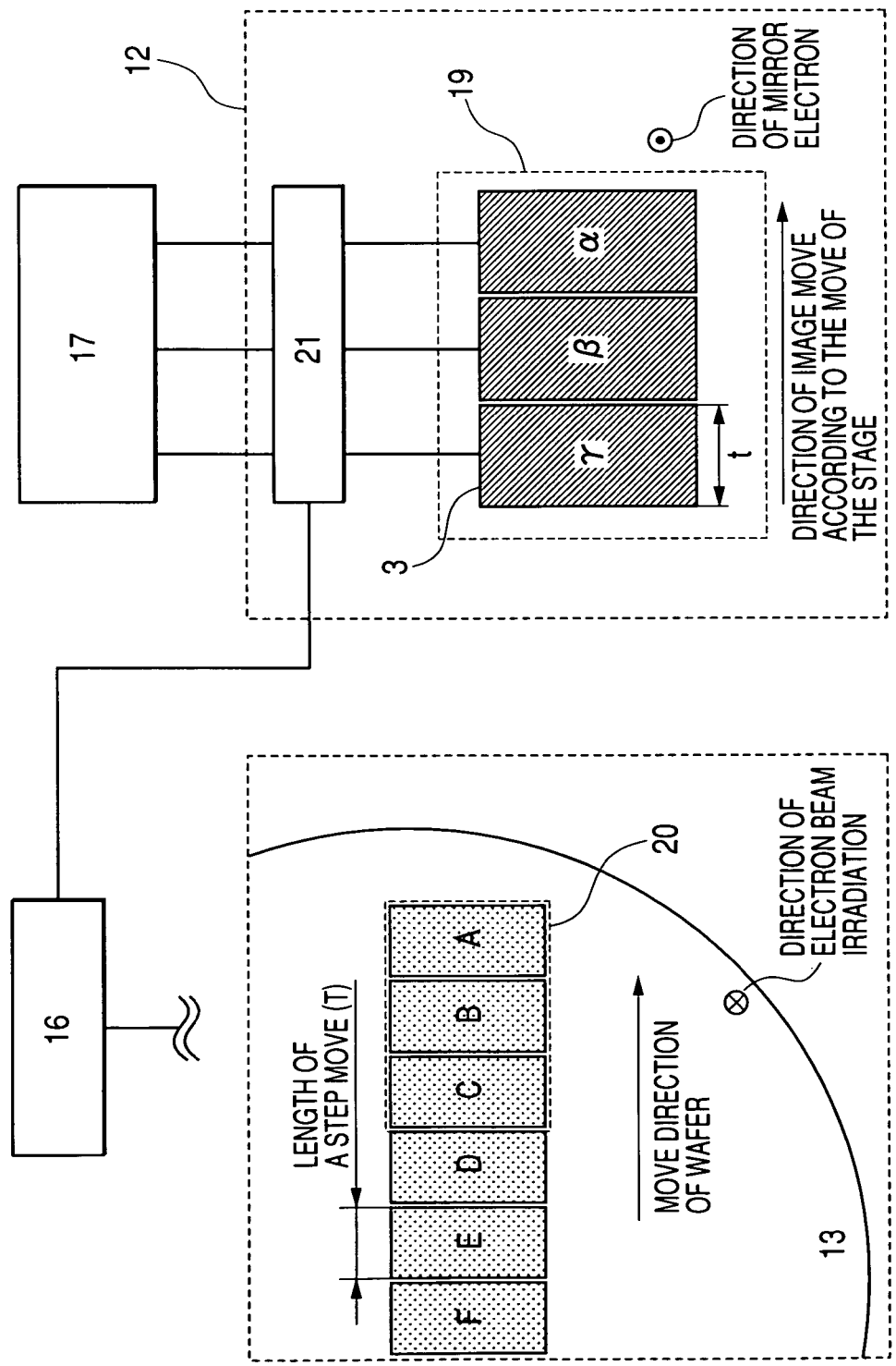
FIG. 5 is a schematic diagram illustrating the method of image capturing by using an image detection device according an embodiment of the present invention.

With reference to FIG. 1 and FIG. 5, the means to acquire images of different focuses for the same portion in a pattern on the wafer 13 will be described. The wafer 13 is placed on a wafer holder 34 on a stage 33; the wafer holder 34 can move two-dimensionally within a plane perpendicular to the direction of the electron beam applied to the wafer 13 so as for the electron beam to be applied all over the surface of the wafer 13. The detector 19 is placed in a manner to be in different distances from the wafer 13 along the direction in which the mirror electron 1 travels, and the detecting planes $\alpha$, $\beta$, $\gamma$ are constructed in such a manner as each of the planes is placed at different height perpendicularly from the surface of the drawing sheet. Here, the multiple detectors 19 are arranged in line with the direction in which images move on the detector 19 in accordance with the move of the stage 33.

Arranging the detector 19 in this way attains the following advantage when acquiring images.

When capturing or acquiring images, a stage driving unit 32 moves the stage 33 one-dimensionally in step-and-repeat mode, and an image capturing unit 21 and a stage controlling unit 16 operate in synchronization with each other. When an electron beam illuminates a rectangular region 20 on the wafer 13, the detecting planes $\alpha$, $\beta$, $\gamma$ capture respective images of the regions A, B, C on the wafer 13. Then the wafer 13 moves the length (T) that corresponds to the side (t) of the detector 19, thereby for the detecting planes $\alpha$, $\beta$, $\gamma$ to capture the images of the region B, C, D respectively. By repeating this operation, images of three different focuses can be obtained for all over the surface of the wafer 13.

By synchronizing stage movement with image capturing as described above, images for all over the wafer can be obtained effectively and at a high speed.

Figure 6A:
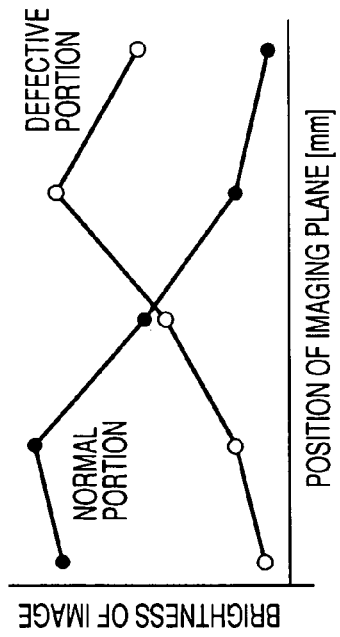
FIGS. 6(a) and 6(b) are schematic diagrams illustrating the image simulation of capturing images of different focuses using an image detection device according to the embodiment of the present invention.
Figure 6C:
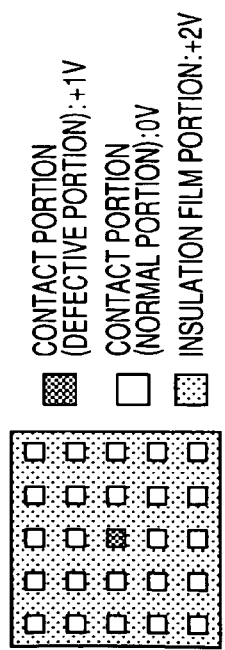
Figure 6B:
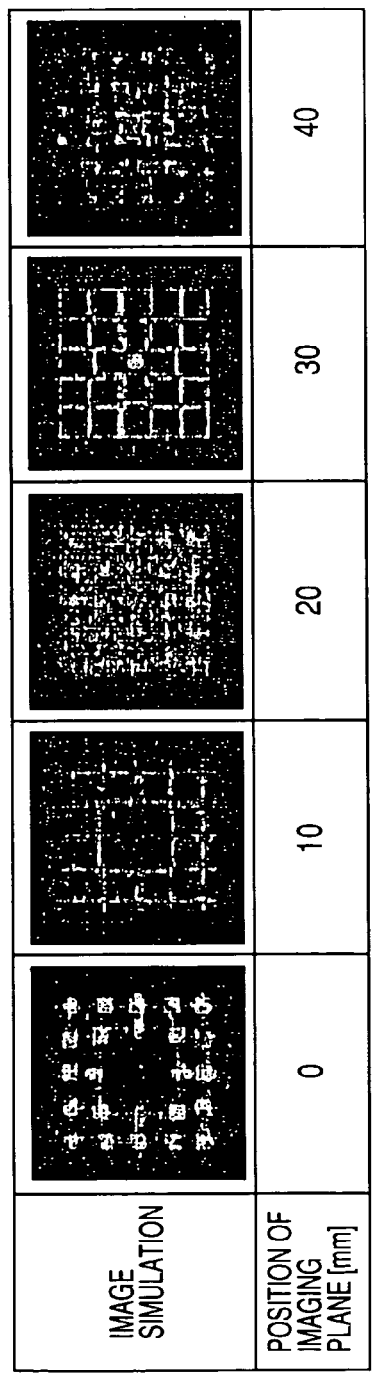

FIG. 6 shows the results of a simulation of obtaining images for the same portion in a pattern on the wafer on different focus conditions by five kinds of detectors 19 that are arranged in different distances from the wafer 13 along the direction in which the mirror electron 1 travels. FIG. 6(a) shows the pattern model of the simulation, FIG. 6(b) shows the images of different focuses obtained as the result of the simulation, FIG. 6(c) is the results of a graphic representation of the relation between the brightness and the forming position (namely the focus) of images for a normal portion 4 and a defective portion 5.

The model in FIG. 6(a) shows a semiconductor pattern produced in a contact process that comprises implanting metal plugs into the contact holes, and then smoothing out by chemical mechanical polishing to the extent that the insulating film is exposed. This pattern consists of 25 contact portions of 0.1 μm square and insulating film portion, with only the contact at the center being charged at +1V, and the other contacts being charged at 0V. And the potential of the insulating film portion is assumed to be +2V evenly all over the region. FIG. 6(b) and FIG. 6(c) are the results of a simulation using the model FIG. 6(a). FIG. 6(b) shows the images obtained when the height of the detection plane 3 is altered incrementally by 10 mm, and FIG. 6(c) shos how the brightness of the images of a normal portion 4 and a defective portion 5 is dependant on their focuses. Here, the height of the detecting plane at which the image is the brightest is different by 20 mm between for the normal portion 4 and the defective portion 5. This shows that the focus conditions for the brightest image of mirror electron 1 from a normal portion 4 and a defective portion 5 are different.

From multiple images of different focuses obtained in this way for an area of a sample, a focusing distance for the region is calculated. For detecting electrical defects, this focusing distance is memorized in the image processing unit 17 as the focusing distance for a standard potential, and for detecting shape defects, this focusing distance is memorized in the image processing unit 17 as the focusing distance for a standard shape characterized by size. And, by calculating focusing distances for other areas of a sample and comparing with the focusing distance for the standard potential or the standard shape, relative potential or shape variance for the other regions can be calculated.

For detecting electrical defects in a semiconductor pattern, the operations described above make clear electrically defective portions in the pattern by calculating the relative potential within a pattern vis-a-vis the potential of the normal portion 4 as the standard potential. Further, since this information on relative potential represents the degree of electrical defect, a database of the information on defective portions and on their relative potential within the surface of a semiconductor wafer 13 may be created, which may be utilized for process monitoring of a semiconductor manufacturing process. Also, this can equally be applied to shape defects.

Second Embodiment

First Embodiment described above explained capturing images step-by-step by controlling the move of the stage 33 in a step-and-repeat mode. The present invention can also be applied to the case of continuously moving the stage 33 at a constant speed and continuously capturing the images by using TDI (Time Delayed Integration) sensors.

The conceptual operation of the TDI sensor will be described with reference to FIG. 7. The TDI sensor operates in such a manner as a charge generated according to the intensity of light received in each light-receptive field is moved along the line in the x direction, and, concurrently, charges generated according to the intensity of light received at the positions after movement are sequentially added up. And the accumulated charge is outputted outside as an electrical signal when the light reaches the end line of the light-receptive plane. Therefore, by keeping the speed at which charges move in the direction of x the same as the speed at which images move on the light-receptive plane, the signals generated during the movement of the images on the sensor are integrated and outputted.

By synchronizing the move of the stage and the speed of TDI sensor's signal integration, it becomes possible to move the stage continuously and at a constant speed and to capture images. Differently from the case of controlling the stage in a step-and-repeat mode, the time of the stage's stand still is shortened, and thereby a dramatic improvement of the inspection speed is realized.

Third Embodiment

First Embodiment and Second Embodiment illustrated an inspection model using the detector 19 having detecting planes 3 at different distances from the surface of the wafer 13 along the travel direction of the mirror electron 1. When conducting an inspection using this method of obtaining images, it is required to place the detection planes 3 at different positions where images move in accordance with the move of the stage 33, and for the application to the inspection of various defects, it is also desirable to be able to optionally or discretionally adjust the height of the detector 19 itself. It is because, for a practical inspection, there are cases where the direction of the move of the stage is altered depending on the layout of a pattern, but with the First and Second Embodiments described above, the alignment of the detectors is limited to one variety, and an inspection can not be he preformed when the direction of the stage's move is altered.

The present embodiment describes the manner of operation of an apparatus in which are provided a rotation-adjustment mechanism thereby to place the detection plane 3 at different positions in the direction of the movement of the image on the detection plane 3, and a mechanism to enable a discretional adjustment of the height of each detector 19.

Figure 8A:
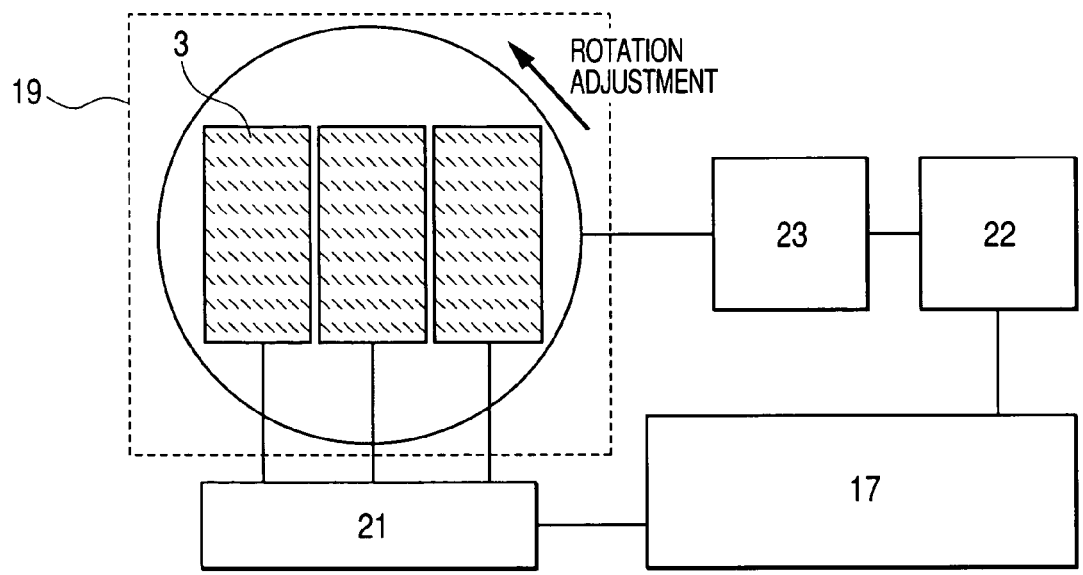
FIGS. 8(a) and 8(b) are diagrams illustrating a detector capable of the rotation adjustment and the relative distance adjustment.
Figure 8B:
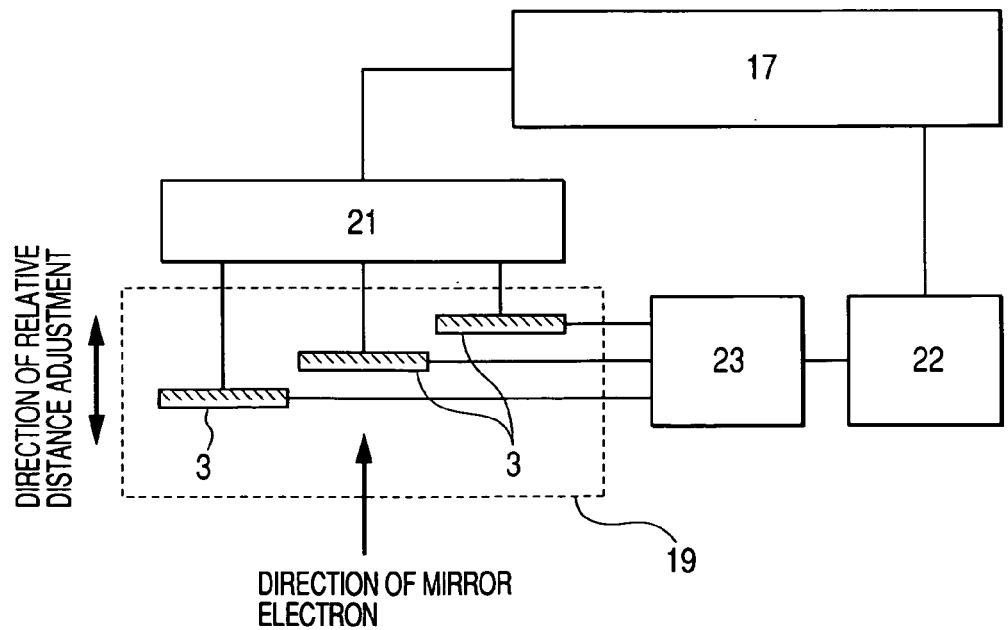

FIG. 8(a) shows the detector 19 as viewed from the axis of the direction in which the mirror electron 1 travels, and FIG. 8(b) is the view of the detector 19 seen from the direction perpendicular to the direction in which the mirror electron 1 travels. The image captured at an image capturing unit 21 is transmitted to an image processing unit 17. Based on a image captured, this image processing unit 17 calculates a proper rotation angle and the relative distance (the distance between the surface of the wafer 13 and the detection plane 3 along the direction in which the mirror electron 1 travels, namely, the position of the detector 19), and transmit the information to a detector control unit 22. Then the detector control unit 22 controls a detector driving unit 23 to adjust the rotation angle and the relative distance of the detector 19. Here, for making an adjustment mentioned above, capturing of an image need not be done at every detection plane 3, but making use of any one detecting plane 3 is sufficient.

Figure 9:
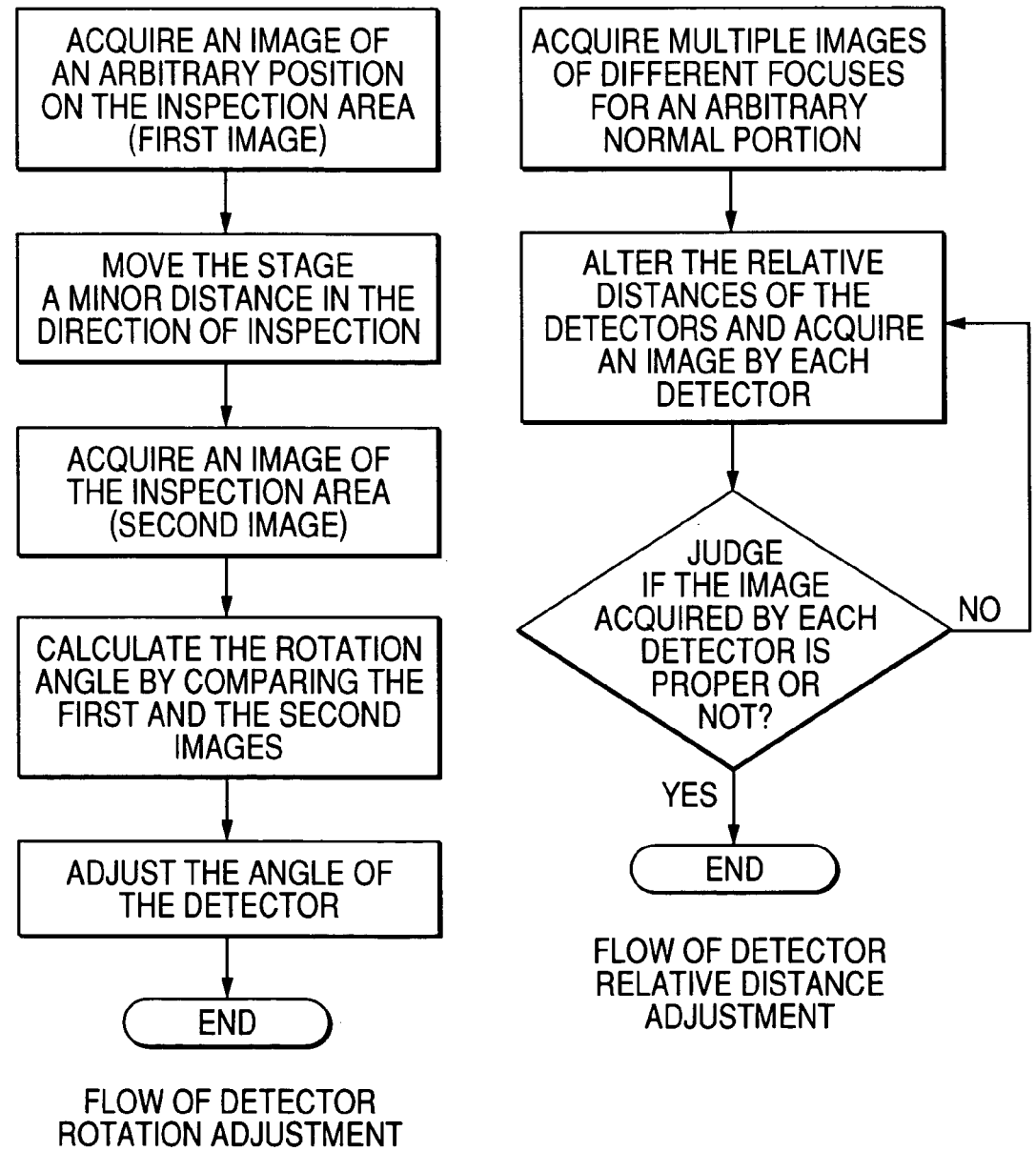
FIG. 9 is a flow diagram illustrating the steps of the rotation adjustments and the relative distance adjustments of a detector by the present invention.

Next, with reference to FIG. 9, the process of adjustment of the rotation angle and the relative distance is explained with a flowchart. For making an adjustment of rotation, in order to check the direction of an image's move on the detection plane 3 in accordance to the move of the stage 33, an image of an arbitrary position on the sample is acquired. Then, the stage 33 is moved a minor distance in the direction of the next inspection area, another image is acquired, and an adjustment angle is calculated from these two images. Based on this adjustment angle, the detector 19 is rotated for an adjustment so that the direction of the move of the stage 33 matches the direction of the alignment of the detection plane 3.

The relative distance of the detector 19 is calculated based on images of different focuses of a normal portion 4 which is arbitrarily designated in the inspection area by an operator of the apparatus. Images of different focuses are acquired through stepwise alteration of the position of the detection plane 3; the image processing unit 17 calculates a proper relative distance; and the position of each detector 19 is adjusted. Here, as for the proper relative distance, for the purpose of detecting minute shape defects or electrical defects, a proper condition is that the contrast of the normal portion 4 is discernible for all the multiple images of different focuses, and a change in the brightness of the normal portion 4 corresponding to the change in focus is discernible. On the other hand, for the purpose of detecting only prominent defects, a proper condition is that a change in the brightness of the normal portion 4 corresponding to the change in focus is indiscernible, that is, there is no contrast discernible of the normal portion 4.

The rotation adjustment as described above enables inspection by moving the stage one dimensionally in an arbitral direction, and the arbitral adjustment of the height of the detection plane 3 enables inspection by arbitrarily changing the focus. Provided with these functions, inspection of all kinds of semiconductor patterns will be enabled.

Forth Embodiment

In the present embodiment, a defect inspection apparatus is described wherein, by altering magnetization of the multiple lenses to form an image of an electron beam drawn back on the surface of a sample, images of different focuses of an inspection area are or acquired captured. In First, Second and Third Embodiments, the position of the detection plane 3 of an image capturing device is altered. An equivalent effect can be obtained when focuses are altered by using optical lens in the imaging unit 38.

Figure 11:
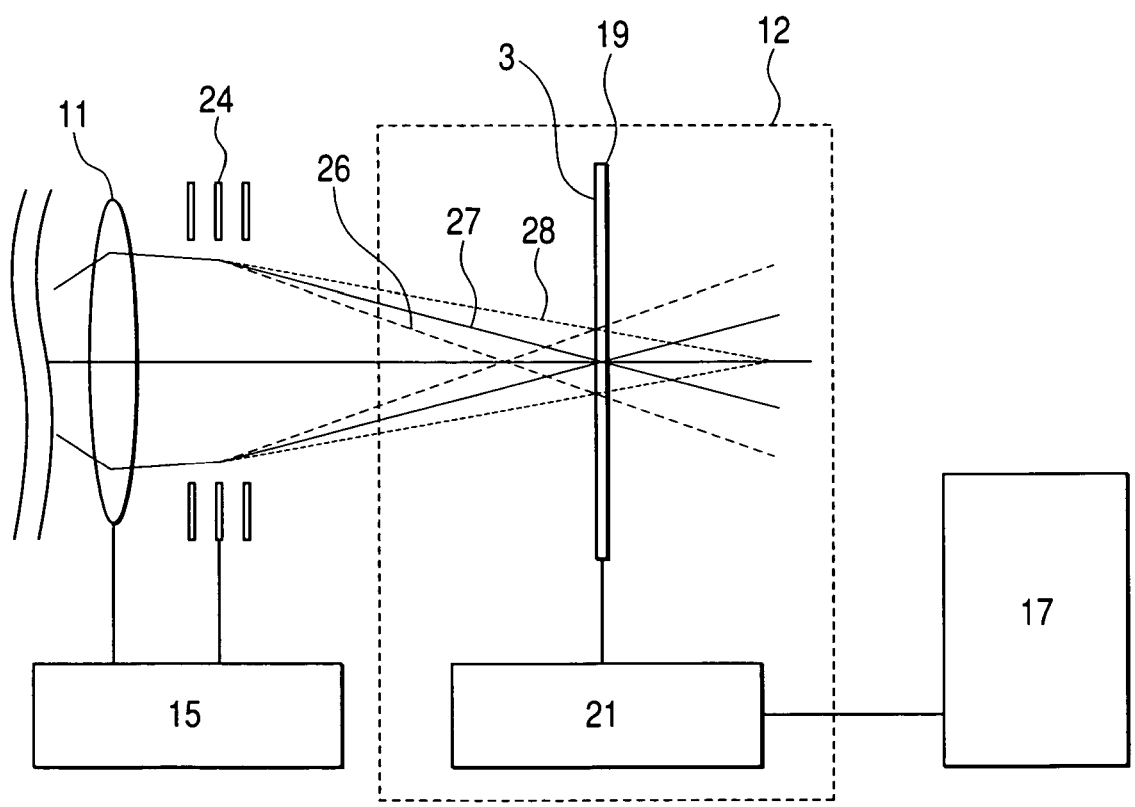
FIG. 11 is a flow diagram illustrating the basic configuration of Fourth Embodiment of the present invention.

An embodiment wherein the detector 19 consists of a single detection plane 3 is illustrated with reference to FIG. 11. FIG. 11 schematically shows a part of the imaging unit 38 (as shown in FIG. 1) of the present invention, the last stage comprising the projection lens and so forth, which comprises mainly the projection lens 11, a variable-focus lens 24 composed of electrostatic lenses, a lens controlling unit 15 to control those lenses, a detector 19, an image capturing unit 21 and an image processing unit 17. In this embodiment, since only an image on one focus condition is obtainable in one operation, in order to obtain an image of a different focus, it is necessary to obtain an image of the same area again by altering the focus. Further, the figure shows the trajectory of the mirror electron 1 that is drawn back at the defective portion 5 and the trajectory of the mirror electron 1 for the normal portion 4 is not shown in the figure. The trajectories a~c (26~28) of the mirror election 1 for the defective portion 5 is the trajectory in case the focus is altered by the variable-focus lens 24. By altering the excitation of the variable-focus lens 24 to get different focus conditions, the same effect as in First, Second and Third Embodiments is obtained.

Figure 10:
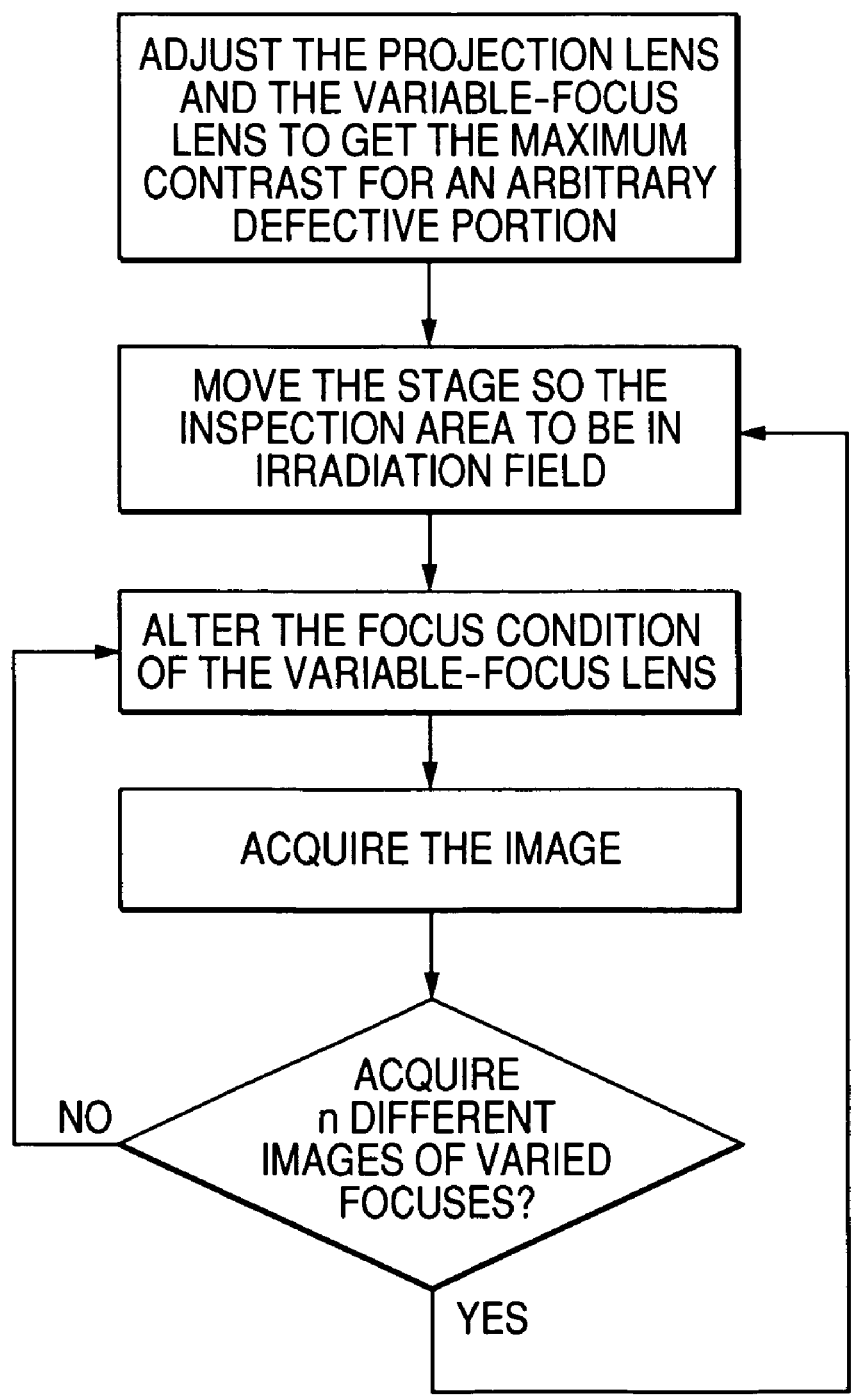
FIG. 10 is a flow diagram illustrating the steps of operation of Fourth Embodiment of the present invention.

FIG. 10 is a flowchart for conducting an inspection of a semiconductor pattern by the configuration described above. First, adjust the focus condition, using the projection lens 11 and the variable-focus lens 24 so as to get the maximum contrast for an arbitrary defective portion 5. Next, move the stage 33 to move the inspection area. For obtaining the images of n number of different focuses, image capturing operation will be conducted by altering the variable-focus lens 24 for n stages, and then move the stage 33 to the next inspection area, conducting an image capturing operation likewise.

The above description exemplifies the case of altering focuses by the variable-focus lens 24. Altering focuses using any optical lens in the imaging unit 38 including objective lens 7 would not affect the advantageous effect of the present invention.

In the case of First, Second and Third Embodiments, while they can realize a very high-speed inspection apparatus, their configurations tend to be complex, making the equipment expensive. The method of the present embodiment enables easy obtainment of images of different focus and provides less expensive working of the present invention.

Fifth Embodiment

Figure 12:
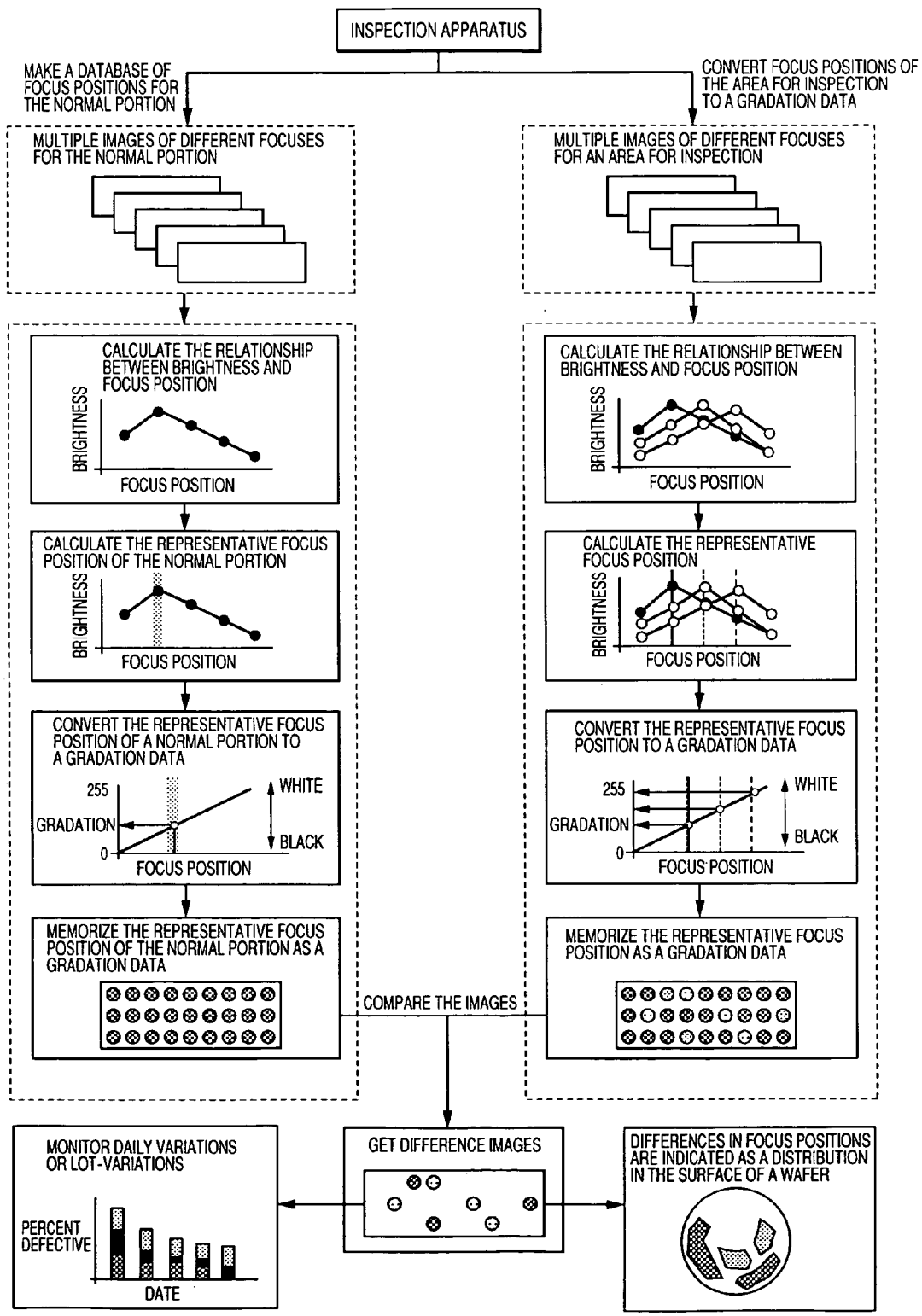
FIG. 12 is a flow diagram illustrating the image processing of an embodiment of the present invention.

With a mirror projection inspection apparatus, it plays a very important role in inspection to obtain multiple images on different focus conditions. First Embodiment described a means to calculate the difference in the focus position of an inspection area based on the images of different focuses. In the present embodiment, process management utilizing information on focus positions in case the present invention is applied to a semiconductor manufacturing process is described with reference to FIG. 12. Here, the differences in the focus positions correspond to the degree of resistance defects when the attention is on electrical defects, and to the degree of size-variation of shape defects when the attention is on shape defects.

First, multiple images of the normal portion 4 of different focuses are obtained, and based on the images, the relationship between the brightness and the focus of the normal portion 4 is calculated. Here, the focuses have been converted to information on relative focus positions of the detector 19. Next, the focus position where the normal portion 4 is brightest is defined as the representative focus position of the normal portion 4. Then the representative focus position is converted to a gradation data and the gradation is memorized. A way to memorize the data may be, if e.g. in 8 bit gradation, defining 0 for black, 255 for white, to memorize it as two-dimensional brightness map, for an easy reference to the database by an operator.

In an actual inspection, obtaining multiple images of different focuses for an inspection area, and calculating the representative focus position based on the images by the same steps described above, they are memorized as a gradation data. Then comparing the data with the standard database for the normal portion 4 initially obtained, the location of defective portion 5 and its degree are calculated. For example, if the gradation data is memorized as a two-dimensional brightness map, difference images are formed from the brightness map of an inspection area and the database for the normal portion 4, and are memorized as the result of an inspection. Now, the difference images themselves represent a defects distribution and the degree of the defects in the inspection area. Here, if the inspection results are memorized in 8-bit data as described above, the data volume may become huge, therefore, recording in lower level of gradation to reduce the data volume would be more convenient.

An inspection result will be made visible by e.g. outputting the data recorded as described above on to an image display unit 42, enabling identification of a distribution defects and their scales (e.g. scales or degrees of resistance defects for electrical defects, and scales or degrees of size-variation for shape defects).

Further, memorizing the inspection results, keeping record of daily variations or lot-variations will facilitate the management of process condition.

As a specific example, management of dry-etching process will be illustrated below:

Generally in the development stage of a dry-etching process, the process optimization is sought by varying several etching conditions (such as, gas flow level, control voltage, etching duration, etc.).

On this occasion, a wafer produced under each condition is inspected by using an inspection apparatus embodying the present invention, and the relation between a dry-etching condition and a defect distribution generated in the surface of a wafer and the scale or degree of the defects is memorized as a database in the image processing unit 17.

In using for the process management at the stage of quantity production, the condition of the dry-etching process is managed based on the database produced at stage of development. For example, from the distribution of defects within the surface or the scale or degree of resistance defects for the defective portion, by finding out which situation in the database it is close to, a problem area can be identified.

By using an inspection apparatus embodying the present invention for process management, an early discovery of a problem in a process and an early estimation of the cause of defects occurrence will be enabled, leading to an improvement of reliability of semiconductor products.

While the invention has been described with respect to a limited number of embodiments, those skilled in the art, having benefit of this disclosure, will appreciate that other embodiments can be devised which do not depart from the scope of the invention as disclosed herein. Accordingly, the scope of the invention should be limited only by the attached claims.

What is claimed is:

1. An inspection apparatus comprising:
    an electron emitting unit for sequentially emitting an electron beam in a direction of an inspection area of a sample;
    a decelerating means for drawing back the electron beam in the vicinity of the inspection area;
    an imaging unit for forming images of the electron beam, which has been drawn back in the vicinity of the inspection area, on multiple different image forming conditions;
    an image detecting unit for capturing the electron beam that formed an image corresponding to each image forming condition; and
    an image processing unit for comparing the images on different image forming conditions with one another to thereby detect a defect in the inspection area.

2. An inspection apparatus according to claim 1, wherein the image detecting unit has multiple detecting planes at different distances from the surface of the sample along the travel direction of the electron beam, and captures the images of the inspection area by using one of the different detecting planes for one of the image forming conditions.

3. An inspection apparatus according to claim 2, further comprising a movable sample stage on which the sample is placed, wherein the multiple detecting planes are arrayed in a direction that the image on the detecting plane moves in accordance with the move of the stage.

4. An inspection apparatus according to claim 3, wherein the multiple detecting planes rotate in the planes that are parallel with the detecting planes.

5. An inspection apparatus according to claim 3, wherein the multiple detecting planes are Time Delayed Integration sensors.

6. An inspection apparatus according to claim 2, wherein the distances of the multiple detecting planes from the surface of the sample along the direction in which the electron beam travels are respectively adjustable.

7. An inspection apparatus according to claim 1, wherein the imaging unit has an excitation variable lens, and, by varying the excitation of the lens, the image forming conditions are varied.

8. An inspection apparatus according to claim 1, wherein the sample is a semiconductor wafer; the inspection area is an area of a circuit pattern; and a defect is a physical defect or electrical defect in the circuit pattern.

9. An inspection apparatus according to claim 1, wherein the electron emitting unit comprises:
    an electron gun for generating an electron beam;
    multiple electrostatic lenses or electro-magnetic lenses for converging the emitted electron beam;
    and the apparatus further comprises a beam separator for separating the beam applied to the sample and the beam drawn back;
    and the imaging unit comprises multiple electrostatic lenses or electro-magnetic lenses for forming an image of the drawn back electron beam.

10. An inspection apparatus according to claim 1, further comprising a cathode other than the electron emitting unit or an optical source, wherein
    an electron beam emitted from the cathode other than the electron emitting unit or light emitted from the optical source is used to control the charge of the sample.

11. An inspection apparatus according to claim 1, further comprising:
    a sample stage that mounts the sample, wherein the sample stage can be applied a voltage thereby to draw back the electron beam incident on the sample.

12. An inspection apparatus according to claim 11, wherein the sample stage is capable of moving at a speed synchronized with a speed of an image capturing speed of the image detecting unit.

13. An inspection apparatus according to claim 1, wherein the image processing unit calculates, by comparing multiple images on the different image forming conditions for one of the inspection areas, the focusing distance of the inspection area.

14. An inspection apparatus according to claim 13, wherein the image processing unit calculates the focusing distance of said one of the inspection areas of the sample as the focusing distance for a standard potential, and, by comparing the focusing distance for the standard potential with the focusing distances for other areas of the sample, calculates the relative potential of the other areas of the sample.

15. An inspection apparatus according to claim 14, wherein said one of the inspection areas of the sample is a normal portion of a semiconductor pattern and the other areas of the sample are the defective portions of the semiconductor pattern.

16. An inspection apparatus according to claim 15, further comprising an image displaying unit,
    wherein the image processing unit outputs to the image displaying unit the distribution of the defective portions calculated from the standard potential and relative potentials, and the relative potentials of the defective portions.

17. An inspection apparatus according to claim 16, wherein the image processing unit memorizes as a database the distribution of the defective portions and the relative potentials of those defective portions, and, by comparing the database with a distribution of defective portions of other semiconductor pattern, an inspection of the quality of the other semiconductor pattern may be conducted.

18. An inspection apparatus according to claim 1, further comprising an image displaying unit, wherein the image processing unit outputs to the image displaying unit each of the images formed on different image forming conditions.

19. An inspection apparatus according to claim 1, wherein the image forming condition is the focus.

20. An inspection method using an inspection apparatus comprising:
    a stage for holding a sample;
    an electron beam source for emitting an electron beam towards the sample holding stage;
    a decelerating means capable of decelerating the electron beam;
    a lens capable of forming an image of the electron beam;

a detector having a detecting plane capable of detecting the electron beam;

an image capturing unit for capturing as an image the electron beam detected by the detector; and an image processing unit for processing the image captured;

wherein the method comprises the steps of:

emitting an electron beam in the direction of a sample;

drawing back the electron beam using the decelerating means;

forming images of the drawn-back electron beam on the image forming planes as multiple images based on multiple image forming conditions;

comparing the multiple images formed on multiple image forming conditions; and detecting the defects of the sample.

21. An inspection method for inspecting the sample according to claim 20 by using images of the electron beam which was emitted toward a sample and then drawn back in the vicinity of the sample, wherein, a focusing distance of the electron beam drawn back from the vicinity of an area of the sample is calculated as the focusing distance for a standard potential; and by comparing the focusing distance for the standard potential with focusing distances of the electron beams drawn back in the vicinity of other areas of the sample, the potentials of the other areas of the sample relative to the standard potential are calculated.

22. An inspection method according to claim 21, wherein the sample is a semiconductor wafer and the relative potential reflects a shape defect or an electrical defect in a circuit pattern on the semiconductor wafer.

23. An inspection method according to claim 21, further comprising, memorizing as a database the relative potential and the distribution of the relative potential in the surface of the sample;

using the result of comparison of the relative potential and the distribution of the relative potential in the surface of another sample with the database, wherein the quality of the other sample is inspected.

24. A process management method for finding out a trouble in a mass production process of a sample using the result of an inspection of the quality of the sample described in claim 23.

25. An inspection apparatus comprising:

a sample stage that mounts a sample to be inspected, an electron optical system which directs electrons to the sample;

a power supply capable of applying a voltage to the sample stage thereby to draw back the electron beam incident on the sample; and an imaging optical system that detects images of the drawn back electron beam;

wherein said imaging optical system is arranged to form the images on a plurality of image forming conditions; and wherein the sample is inspected based on the detected images.

26. An inspection apparatus according to claim 25, wherein the imaging optical system has an imaging unit that forms images of the drawn back electron beam on a plurality of image forming conditions.

27. An inspection apparatus according to claim 25, wherein the imaging optical system has an image detecting unit for capturing the electron beam that has formed an image according to each image forming condition.

28. An inspection apparatus according to claim 26, wherein the imaging unit has an excitation variable lens, and, by varying the excitation of the lens, the image forming conditions are varied.

29. An inspection apparatus according to claim 27, wherein the image detecting unit has a plurality of detecting planes at different respective distances from the surface of the sample along the travel direction of the electron beam, and captures the images of the inspection area by using one of the different detecting planes for each of the image forming conditions.

30. An inspection apparatus according to claim 25, wherein the electron optical system comprises:

an electron gun for generating an electron beam;

a plurality of electrostatic lenses or electro-magnetic lenses for converging the emitted electron beam; and the apparatus further comprises a beam separator for separating the beam applied to the sample and the beam drawn back.

31. An inspection apparatus according to claim 25, further comprising an image processing unit for comparing the images on different image forming conditions with one another to thereby detect a defect in the sample.

32. An inspection apparatus according to claim 25, further comprising an image displaying unit which displays each of the images formed on different image forming conditions.

33. An inspection apparatus comprising:

a sample stage for holding a sample;

an electron beam source for emitting an electron beam towards the sample stage;

a power supply capable of applying a voltage to the sample stage thereby to draw back the electron beam incident on the sample;

a lens capable of forming an image of the drawn back electron beam;

a detector having a detecting plane capable of detecting the drawn back electron beam on a plurality of image forming conditions; and an image processing unit that identifies defective portions at the sample based on the detected signal from the detector.

* * * * *